United States Patent [19]

Fukuhara et al.

[11] Patent Number: 5,017,729

[45] Date of Patent: May 21, 1991

[54] PHENOL PREPARATION PROCESS AND PROPYLENE RECOVERY THEREFROM

[75] Inventors: Hiroshi Fukuhara; Fujihisa Matsunaga, both of Chiba, Japan

[73] Assignee: Mitsui Petrochemical Industries, Ltd., Tokyo, Japan

[21] Appl. No.: 402,528

[22] Filed: Sep. 5, 1989

[30] Foreign Application Priority Data

Sep. 30, 1988 [JP] Japan ................................ 63-246658

[51] Int. Cl.$^5$ ..................... C07C 37/08; C07C 45/53
[52] U.S. Cl. ........................... 568/798; 568/385; 568/565; 568/569; 568/577; 568/741; 568/768; 568/799; 568/840; 585/422; 585/446
[58] Field of Search .............. 568/385, 565, 569, 577, 568/741, 768, 795, 798, 799, 840, 638; 585/446

[56] References Cited

U.S. PATENT DOCUMENTS

| | | | |
|---|---|---|---|
| 4,260,845 | 4/1981 | Shioyama | 585/640 |
| 4,310,712 | 1/1982 | Langley | 568/798 |
| 4,431,849 | 2/1984 | Colvin | 568/798 |
| 4,876,397 | 10/1989 | Knifton et al. | 568/798 |
| 4,906,790 | 3/1990 | Ishiguro et al. | 568/798 |

FOREIGN PATENT DOCUMENTS

| | | | |
|---|---|---|---|
| 25653 | 3/1970 | Japan | 568/798 |
| 62-12729 | 6/1987 | Japan | 568/840 |
| 62-77338 | 9/1987 | Japan | 568/840 |
| 8702910 | 5/1987 | PCT Int'l Appl. | |
| 1207133 | 9/1970 | United Kingdom | 568/798 |

OTHER PUBLICATIONS

Gasior et al., Chemical Abstracts 38862z, vol. 101, No. 6 of Aug. 6, 1984.

*Primary Examiner*—Werren B. Lone
*Attorney, Agent, or Firm*—Nixon & Vanderhye

[57] ABSTRACT

Phenol is produced in a recycle manner by (a) reacting benzene with propylene to synthesize cumene, (b) oxidizing the cumene of step (a) into cumene hydroperoxide, (c) acid cleaving cumene hydroperoxide into phenol and acetone, (d) hydrogenating the acetone of step (c) into isopropanol, (e) dehydrating the isopropanol of step (d) into propylene, and (f) recycling the propylene of step (e) to step (a). It is also possible to take propylene from step (e). The acetone by-product produced upon preparation of phenol is converted into propylene which is useful by itself for any other uses or recycled to the phenol producing process.

5 Claims, No Drawings

PHENOL PREPARATION PROCESS AND PROPYLENE RECOVERY THEREFROM

BACKGROUND OF THE INVENTION

This invention relates to the preparation of phenol, and more particularly to a phenol preparing process which can recover propylene from the acetone by-product and recycle the recovered propylene as the starting material.

It is well known in the art to react benzene with propylene to produce cumene, to oxidize cumene to produce cumene hydroperoxide, and to acid cleavage cumene hydroperoxide into phenol and acetone. A conventional phenol preparing process having these steps combined is generally known as the cumene process.

It is also an old well-known technique to hydrogenate acetone into isopropanol. This technique is still widely used at present for the assay of the catalytic activity of a hydrogenating catalyst and other purposes. For example, the activity of Raney nickel catalysts is often examined by comparing their acetone hydrogenating ability. Several advanced processes have been proposed as disclosed in Japanese Patent Application Kokai Nos. 12729/1987 and 77338/1987.

Nevertheless, insofar as the inventors know, it has never been proposed to produce isopropanol from the acetone by-product resulting from preparation of phenol by the cumene process, and to dehydrate the isopropanol into propylene.

There are known some analogous processes, for example, to produce ethylene from ethanol and to produce isobutylene from tert.-butanol. However, these olefin producing processes cannot be applied to the production of propylene from isopropanol for the following reason. Since propylene is substantially different in reactivity from ethylene or isobutylene, those skilled in the art cannot presume the dehydration of isopropanol from either the conditions for synthesis of ethylene from ethanol or the conditions for synthesis of isobutylene from tert.-butanol.

As to the reuse of the acetone which is by-produced in the cumene process, for example, by its conversion into propylene, no useful proposals have been made.

The phenol preparing process generally known as the cumene process is characterized by the production of acetone by-product, which is advantageous from some aspects, but disadvantageous from other aspects. More particularly, it is an advantage in that simultaneous production of two products in a single preparation unit is more efficient than individual production in separate units. In turn, if the proportion of phenol and acetone produced is unbalanced relative to their commercial demands, one for less demand is produced largely in vain.

As is known in the art, acetone is available in surplus for these years. Thus the production of acetone by-product is now considered as a serious drawback of the cumene process. Although acetone has found the majority of its application as a starting material for preparing methyl methacrylate, the demand for acetone is decreasing because of a switch of the starting material for preparing methyl methacrylate to another.

Under the circumstances, there is a need for the development of a phenol preparing process which is devoid of production of acetone and other by-products. Although several proposals have been made, there is available no process capable of preparing phenol in satisfactory yields.

In addition, impurities in propylene often cause a drawback during the preparing step of cumene from benzene and propylene in the cumene process for the preparation of phenol. That is, propylene for use in the cumene preparation is manufactured generally using crude oil as the starting material. Crude oil, however, contains sulfur compounds and various heavy metals, and these impurities are sometimes carried in propylene as trace contaminants during its manufacturing process. For example, carbonyl sulfide (COS) as a sulfur compound or As as a heavy metal contaminant in propylene inhibits function of a catalyst (aluminum chloride-HCl complex) for use in the cumene preparation, thus disturbing normal progress of the cumene synthesis. Therefore, a strict purification process is perproduced to avoid contamination of propylene with these impurities. Types and quantity of these contaminants, however, vary depending on not only the crude oil source but also the difference in the process conditions for the preparation of propylene from crude oil. Such irregularity burdens the propylene purification process with exceptionally complex and severe steps.

In consequence, a process for the preparation of propylene with highly stable purity containing no such impurities has been expected to be established, for the purpose of reducing the extreme burden of steps in the propylene purification process.

SUMMARY OF THE INVENTION

Therefore, an object of the invention is to provide a novel and improved process for preparing phenol in commercially satisfactory yields without producing by-products.

The outstanding problem of the cumene process is the production of large amounts of acetone by-product, but not the low percent yield of phenol produced. To overcome the problem, the inventors have developed a process capable of converting the acetone by-product into propylene, that is, a process capable of obtaining propylene upon preparation of phenol. By incorporating this process into the phenol preparing process, the inventors have reached a process for preparing phenol without producing acetone by-product.

Moreover, the propylene preparation obtained by dehydrating isopropanol which has been converted from acetone by means of hydrogenation does not contain any of the above-cited sulfur compounds and heavy metals. Purity of the propylene, therefore, is high enough to be used as the raw material for cumene synthesis. Such a high purity renders possible reduction of the burden of steps in the propylene purification process to a high degree and, in consequence, sharp industrial rationalization of the cumene preparation process.

The above and other objects can be achieved according to the present invention by cooperatively combining the following steps.

According to a first aspect of the invention, there is provided a process for preparing phenol, comprising the steps of:

(a) reacting benzene with propylene to synthesize cumene, (b) oxidizing the cumene of step (a) to convert it into cumene hydroperoxide, (c) acid cleaving cumene hydroperoxide into phenol and acetone, (d) hydrogenating the acetone of step (c) to convert it into isopropanol, (e) dehydrating the isopropanol of step (d) into propylene, and (f) recycling the propylene of step (e) to step (a).

According to a second aspect of the invention, there is provided a process for recovering propylene from the acetone by-product produced upon preparation of phenol, comprising the steps of:

(a) reacting benzene with propylene to synthesize cumene, (b) oxidizing the cumene of step (a) to convert it into cumene hydroperoxide, (c) acid cleaving cumene hydroperoxide into phenol and acetone, (d) hydrogenating the acetone of step (c) to convert it into isopropanol, and (e) dehydrating the isopropanol of step (d) into propylene.

According to the process of the invention, phenol can be produced from benzene, oxygen, and hydrogen using a hydrocarbon having 3 carbon atoms as an interlocking element.

DETAILED DESCRIPTION OF THE INVENTION

In the practice of the invention, steps (a), (b), and (c) may be in accord with the conventional well-known cumene process.

One typical example of the cumene process will be described.

(a) Step of reacting benzene with propylene to synthesize cumene

Benzene is reacted with propylene in the presence of a catalyst such as aluminum chloride complex. The aluminum chloride complex is prepared by causing aluminum chloride to absorb gaseous hydrogen chloride in a solvent such as cumene.

The molar ratio of benzene to propylene is preferably in the range of from 1/1 to 10/1, more preferably from 1.2/1 to 6/1. The catalyst or aluminum chloride complex is preferably present in an amount of about 0.01% to 5% by weight, more preferably about 0.1% to 1% by weight of aluminum chloride based on the reactants. For this reaction, hydrogen chloride gas may be co-present in the reaction system in order to stabilize the complex catalyst.

The alkylation to produce cumene preferably takes place at a temperature of from 30° C. to 200° C., more preferably 60° C. to 160° C. under a pressure of from atmospheric pressure to 15 kg-f/cm². The reaction may be carried out in a batchwise, continuous, or semi-batchwise manner.

The alkylation partially yields higher alkylated by-products in addition to the end product or cumene. The reaction mixture resulting from alkylation is thus subject to distillation to separate the mixture into unreacted benzene, cumene, and higher alkylated products. The unreacted benzene and higher alkylated products are recycled to the alkylation step and subjected to alkylation again.

(b) Step of oxidizing the cumene of step (a) into cumene hydroperoxide

Oxidation of cumene is carried out at a temperature of about 60° C. to 150° C., preferably about 90° C. to 130° C. under a pressure of about 1 to 10 kg-f/cm² using molecular oxygen. The molecular oxygen used herein may be oxygen, air, or a mixture of oxygen diluted with an inert gas.

In order for the oxidation to take place smoothly, an alkaline compound is preferably co-present in the reaction system to adjust the pH of the system to an appropriate level, preferably in the range of pH 8.5 to 10.5. Examples of the alkaline compound include sodium carbonate, potassium carbonate, sodium hydroxide, and potassium hydroxide, all in the produce of aqueous solution. The pH of the reaction system is adjusted throughout the oxidation process by adding the alkaline compound in small increments to the system.

The reaction time for oxidation is not particularly limited and may be selected so as to achieve a maximum selectivity of the end product or cumene hydroperoxide.

An initiator is preferably added to the reaction system to smoothly start oxidation. Examples of the initiator includes azo compounds such as $\alpha,\alpha'$-azobisisobutyronitrile and $\alpha,\alpha'$-azobiscyclohexylnitrile. The cumene hydroperoxide resulting from oxidation of cumene is also a preferred initiator. The initiator is preferably added to the system in an amount of from about 0.1% to 5% by weight, more preferably from about 0.5% to 2% by weight based on the reactants.

The oxidation may be carried out in a batchwise, continuous, or semi-batchwise manner.

(c) Step of acid cleaving cumene hydroperoxide into phenol and acetone

The cumene hydroperoxide is often present in a concentration of about 20% to 30% by weight in the oily phase of the reaction mixture resulting from step (b). The reaction mixture of (b) should preferably be concentrated, as by distillation, so as to increase the cumene hydroperoxide concentration to 60% to 85% by weight before the mixture is subject to acid cleavage. Such concentration may be carried out at a temperature of up to 150° C., preferably up to 120° C., and more preferably up to 100° C. Concentration at too higher temperatures would undesirably cause thermal cleavage of cumene hydroperoxide resulting in a low yield of the end product or phenol. As long as effective concentration is achieved, the temperature is preferably as low as possible for safe handling of peroxide.

An acidic compound is used as the catalyst in the cleavage of step (c). The catalysts used herein include strong acids such as sulfuric acid, perchloric acid, and hydrofluoric acid. Also included are heteropoly-acids such as phosphotungstic acid and phosphomolybdic acid. Solid acids such as ion-exchange resins and silica-alumina may also be used. The catalyst is preferably added in an amount of about 0.01% to 5% by weight, more preferably 0.1% to 2% by weight based on the reaction mixture concentrate.

Also, step (c) uses a solvent as reaction medium. Examples of the solvent include aromatic hydrocarbons such as benzene, toluene, xylene, and cumene; aliphatic hydrocarbons such as hexane, heptane, cyclohexane, and methylcyclohexane; alcohols such as methanol, ethanol, propanol, and butanol; ketones such as acetone, methyl ethyl ketone, and methyl isobutyl ketone; and ethers such as diisopropyl ether and dibutyl ether. Acetone is the most preferred reaction medium because it is produced by the acid decomposition of cumene hydroperoxide. The amount of the solvent used is preferably about 1 to 20 times, more preferably about 2 to 10 times the weight of the reaction mixture concentrate undergoing acid cleavage.

The acid cleavage may be carried out in either a continuous or semi-batchwise manner. Batchwise operation is less desirable because a high concentration cumene hydroperoxide solution can come in contact with the acid catalyst, giving rise to too rapid cleavage.

At the end of acid cleavage, the reaction mixture is subject to concentration to recover the acetone. Part of the recovered acetone is used as the reaction medium for acid cleavage again while the remaining acetone corresponding to the amount produced by acid cleavage of cumene hydroperoxide is delivered to subsequent step (d) for hydrogenating acetone into isopropanol. The concentrate which has been stripped of acetone is subject to precision distillation for recovering the end product or phenol.

(d) Step of hydrogenating the acetone of step (c) into isopropanol

Catalysts, often Raney nickel catalysts are used in the step of hydrogenating acetone into isopropanol. Also useful are nickel, copper-chromium, Raney nickel-copper, copper-zinc and platinum group catalysts known as hydrogenating catalysts, for example, platinum, palladium, ruthenium, rhodium, and similar metals on active carbon, aluminum and other carriers. Preferred catalyst is Raney nickel. The reaction temperature may range from room temperature to 200° C. For a commercially acceptable reaction rate, the reaction temperature may range from 60° C. to 150° C., more preferably from 60° C. to 140° C.

Hydrogenation may be carried out by either liquid or gas phase reaction. Thus the pressure may range from atmospheric pressure to 80 kg-f/cm$^2$, more preferably from 5 to 50 kg-f/cm$^2$. Hydrogen gas is used relative to the acetone reactant in a molar ratio of from 1/2 to 10/1, preferably from 1/1 to 5/1.

The hydrogenation may be carried out in the presence or absence of a reaction medium. Examples of the solvent used herein include alcohols such as methanol, ethanol, propanol, and butanol. Also useful is isopropanol which is a hydrogenation product of acetone. Also useful are glycols such as ethylene glycol, propylene glycol, diethylene glycol, and triethylene glycol; and ethers such as diisopropyl ether, dibutyl ether, ethylene glycol dimethyl ether, diglyme (diethylene glycol dimethyl ether) and triglyme. Aprotic polar solvents may also be used, for example, dimethylformamide, dimethylacetamide, acetonitrile, and dimethyl sulfoxide. Also useful are saturated hydrocarbons such as hexane, heptane, cyclopentane, and cyclohexane. In the practice of hydrogenation, water is also preferred as the solvent.

The hydrogenation step may be batchwise or continuous. Depending on the shape of a particular catalyst used, reaction may be carried out in a fluidized bed using powder catalyst or a fixed bed using granular catalyst. Fixed bed reaction is preferred in view of ease of separation of the catalyst from the reaction mixture and simplicity of the reaction system.

When hydrogenation of acetone is carried out in a fixed bed, hydrogen gas may be contacted with the reaction mixture in either gas-liquid counter flow or gas-liquid parallel flow. The liquid and gas flows may be used in either of liquid down flow-gas up flow, liquid up flow-gas up flow, and liquid down flow-gas down flow modes. To increase reaction rate, the liquid-gas down flow mode known as a trickle bed is preferred.

(e) Step of dehydrating the isopropanol of step (d) into propylene

In dehydrating the isopropanol of step (d) into propylene, a catalyst in the form of an acidic compound may be used. Examples of the catalyst used herein include compounds generally known as acidic materials, for example, mineral acids such as sulfuric acid, phosphoric acid, hydrochloric acid, and nitric acid, halo peroxides such as perchloric acid, perbromic acid, and periodic acid, heteropolyacids such as phosphomolybdic acid, silicomolybdic acid, phosphotungstic acid, and silicotungstic acid. Other useful catalysts are solid acidic materials, for example, ordinary solid acids such as silica, silica-alumina, alumina and γ-alumina and metal oxides such as titanium oxide, zinc oxide, and zirconium oxide. Various zeolites which now draw attention as shape selective catalysts and zeolites modified with metal ions may also be used as the catalyst. Among these catalysts, most preferred are γ-alumina and titanium oxide.

Dehydration of isopropanol may be carried out in either gas or liquid phase. The reaction temperature preferably ranges from about 100° C. to 450° C., more preferably from about 200° C. to 350° C, most preferably from 260° C. to 350° C. The reaction pressure may be reduced, atmospheric, or increased pressure. In the case of liquid phase reaction, the reaction system should be pressurized to maintain the system in liquid phase.

Dehydration is preferred to be carried out under increased pressure, especially within a range under which propylene as the reaction product is obtained in the form of liquid. For example, liquid propylene can be recovered by carrying out the dehydration reaction at an increased pressure of 18 kg/cm$^2$ and then cooling the reaction mixture at 40° C. or less. Because recovery of liquid propylene renders possible recycle of the recovered propylene as starting material of step (a) by directly drying the liquid propylene and recycling the dried propylene to step (a) through step (f). These facilities for the process can be simplified by leaving out booster pump etc. which are essential for the liquefaction of gaseous propylene in the case of gas phase reaction.

In addition, distillation and purification of liquid propylene can be carried out easily as occasion demands.

In the practice of the invention, the isopropanol dehydration step may be either batchwise or continuous. When a solid catalyst is used, reaction may adopt a fluidized bed using powder catalyst or a fixed bed using granular catalyst depending on the shape of a particular catalyst used. Fixed bed reaction is preferred in view of ease of separation of the catalyst from the reaction mixture and simplicity of the reaction system.

In this way, propylene can be recovered from the acetone by-product produced upon preparation of phenol. The thus recovered propylene has a purity of at least about 99.5% and is ready for use as the reactant in step (a) and also useful as the reactant for the synthesis of polypropylene, acrylonitrile, propylene oxide, ethylene-propylene rubber and the like.

(f) Step of recycling the propylene of step (e) to step (a)

In a preferred embodiment, the propylene-containing gas product discharged from the reactor of step (e) is once collected in a gas holder and thereafter pressurized by a booster pump into a pressurized gas having a propylene content of 80% to 99.9%, more preferably 99.5% to 99.9% and a pressure of 10 to 20 kg-f/cm$^2$ before it is recycled to step (a), that is, alkylation step. In an alternative embodiment, the propylene-containing gas product is directly passed through a dry ice trap to collect the liquefied product, which is transferred to a pressure vessel where the temperature is raised to restore the liquefied product to a gaseous state for recycling to the alkylation step.

EXAMPLE

Examples of the invention are given below by way of illustration and not by way of limitation.

Example 1

Alkylation of benzene with propylene

A 1-liter glass autoclave equipped with Teflon-coated agitating blade and a thermometer sheath was charged with 78 grams of benzene and aluminum chloride complex. The amount of aluminum chloride complex charged was 0.08 grams calculated as aluminum chloride, which corresponded to a molar ratio of aluminum chloride complex to propylene of 1/1000. The autoclave was immersed in an oil bath and the interior of the autoclave was maintained at a temperature of 100° C. with thorough stirring.

To the autoclave, 25.2 grams of propylene in gaseous state was admitted in increments. That is, the propylene was supplied over a period of about 90 minutes while the interior pressure of the autoclave was maintained at 3 kg-f/cm². The reaction was terminated at the end of propylene supply, and the reaction mixture was taken out of the autoclave. The reaction mixture was analyzed by gas chromatography to find that it contained 25.1% by weight of cumene, 13.3% by weight of meta-diisopropylbenzene, 7.4% by weight of paradiisopropylbenzene, and 7.9% by weight of triisopropylbenzene. The total yield of cumene, diisopropylbenzenes, and triisopropylbenzene was 99% based on the weight of the propylene feed.

The reaction mixture was separated by distillation into unreacted benzene, cumene, higher isopropylated products. The higher iropropylated products were fed back to the initial or alkylation step for trahsalkylation to convert them into cumene.

Oxidation of cumene

A 500-ml stainless steel autoclave equipped with an air blowing tube, alkali feed port, sampling nozzle, thermometer sheath, reflux condenser, and intensive stirrer was charged with 120 grams of cumene, 30 grams of 5% sodium carbonate aqueous solution, and 0.5 grams of α,α'-azobisisobutyronitrile initiator. The air in the autoclave was purged with nitrogen and the initial pressure was set at 5 kg-f/cm² with nitrogen before heating was started with stirring. When the interior temperature reached 110° C., air blowing was started.

At the same time as the start of air blowing, the revolution of the stirrer was increased to ensure sufficient gas-liquid contact. Cumene was oxidized by blowing air at a rate of 30 1/hr. While the oxidation reaction continued, the reaction mixture was sampled out at intervals through the sampling nozzle to examine the pH of the reaction mixture. Small portions of 5% sodium carbonate aqueous solution were pumped to the reactor through the alkali feed port so as to maintain the reaction mixture at pH 9 to 10.

The reaction was terminated when 10 hours had passed since the start of air blowing. The reaction mixture was taken out of the autoclave and separated into oily and aqueous phases. The oily phase was subjected to liquid chromatography to determine the content of cumene hydroperoxide, finding that the oily phase contained 26% by weight of cumene hydroperoxide.

Acid cleavage of cumene hydroperoxide

The oily phase resulting from oxidation of cumene was concentrated at a temperature of 100° C. and a vacuum of 160 mmHg, distilling off the unreacted cumene. The concentrating operation was stopped when the oily phase was concentrated by a factor of about 3. The oily phase then contained about 78% by weight of cumene hydroperoxide.

A 500-ml four-necked flask equipped with a stirrer, dropping funnel, thermometer sheath, and reflux condenser was charged with 150 ml of acetone and 2 grams of conc. sulfuric acid. The dropping funnel was charged with 100 grams of the cumene hydroperoxide concentrate. The flask was set in a water bath at a temperature of 80° C. to cause the acetone to continuously reflux with stirring the flask contents.

Under acetone reflux, the cumene hydroperoxide concentrate was added dropwise to the flask from the funnel. The rate of addition of the concentrate was adjusted while observing the amount of refluxing acetone. After the entire amount of the cumene hydroperoxide concentrate was added, the reaction was continued for a further 30 minutes. At the end of reaction, the reaction mixture was analyzed by liquid chromatography, finding that little cumene hydroperoxide was left, that is, a conversion of approximately 100%. It was found that phenol was produced in an amount corresponding to 95% of the converted cumene hydroperoxide.

Powder sodium carbonate was added to the reaction mixture to neutralize the sulfuric acid catalyst. The solids were removed from the neutralized reaction mixture by filtration and the filtrate was concentrated to recover acetone. The amount of acetone recovered contained the acetone charge plus 28.5 grams of acetone resulting from acid cleavage of cumene hydroperoxide.

Hydrogenation of acetone

A vertical stainless steel reactor tube having an inner diameter of 1 inch (25.4 mm) and a length of 500 mm was loaded at an intermediate with 100 grams (48 ml) of lumpy Raney nickel alloy (R-20L manufactured by Nikko Rika K.K.). The reaction tube was filled with water and then 20% caustic soda aqueous solution was slowly pumped into the tube to develop the Raney nickel catalyst. The reactor interior temperature rose because the catalyst development produced exothermic heat. The flow rate of the caustic soda solution was controlled such that the reactor interior temperature did not exceed 60° C. After 0.5 liters of the caustic soda solution was pumped, the feed was replaced by water to rinse the reactor filling. Rinsing was continued until the water outflow from the reactor became neutral. At the end of rinsing, the pump feed was replaced by isopropanol to fill the reactor therewith. Heating of the reactor was started.

When the interior temperature reached 100° C., reaction was commenced by feeding acetone and hydrogen into the reactor from its top at a flow rate of 59.0 g/hr. and 40.2 l/hr., respectively. The reactor was maintained at a pressure of 20 kg-f/cm².

The reaction mixture exiting the reactor at the bottom was separated into the reaction liquid and hydrogen gas by means of a gas-liquid separator. The reaction liquid and hydrogen gas were discharged at a flow rate of 60.0 g/hr. and 15.3 l/hr., respectively.

The reaction was continued for 9 hours while acetone and hydrogen were continuously fed. At this point, the reaction liquid and hydrogen gas were respectively analyzed by gas chromatography. It was found that 0.2% by weight of acetone remained in the reaction liquid and the remaining component consisted solely of isopropanol. Analysis of the gas discharge showed the absence of methane, ethane and propane. Reaction efficacy was calculated on the basis of these analytical results, finding that isopropanol was produced in a yield of 99.8%.

Dehydration of isopropanol

A vertical stainless steel reactor tube having an inner diameter of 1 inch (25.4 mm) and a length of 500 mm was loaded at an intermediate with 20 ml of commercially available gamma-alumina finely divided to a size of 8 to 14 mesh. The air in the reactor was purged with nitrogen and the reactor was then heated under a nitrogen pressure of 10 kg-f/cm$^2$.

When the reactor interior temperature reached 320° C., isopropanol was fed to the reactor from its top at a flow rate of 40 ml/hr. The reaction was continued for 8 hours while the reaction pressure was maintained at 10 kg-f/cm$^2$.

A liquid product predominantly comprising water and a gas product predominantly comprising propylene were produced with the progress of reaction in an amount of 9.5 g/hr. and 12.2 l/hr., respectively. The liquid and gas products were analyzed by gas chromatography, finding the reaction result that the isopropanol conversion was 99.6%, and the propylene yield was 99.3%. The gas product contained propylene in a purity of 99.9%.

The resulting gas product, that is, propylene was ready for recycle to the benzene alkylation step without special purification.

Alkylation using the gas product from isopropanol dehydration

A 1-liter glass autoclave equipped with a Teflon-coated agitating blade and a thermometer sheath was charged with 78 grams of benzene and aluminum chloride complex. The amount of aluminum chloride complex charged was 0.08 grams calculated as aluminum chloride, which corresponded to a molar ratio of aluminum chloride complex to propylene of 1/1000. The autoclave was immersed in an oil bath and the interior of the autoclave was maintained at a temperature of 100° C. with thorough stirring.

To the autoclave, the gas product resulting from the previous dehydration of isopropanol (which was collected by liquefying in a dry ice trap) was admitted in increments while the interior pressure of the autoclave was maintained at 3 kg-f/cm$^2$. The gas product was supplied over a period of about 90 minutes in an amount corresponding to 25.2 grams of propylene. The reaction was then terminated. The reaction mixture was taken out of the autoclave and analyzed by gas chromatography to find that it contained 25.1% by weight of cumene, 13.3% by weight of meta-diisopropylbenzene, 7.4% by weight of para-diisopropylbenzene, and 7.9% by weight of triisopropylbenzene. The total yield of cumene, diisopropylbenzenes, and triisopropylbenzene was 99% based on the weight of the propylene feed.

It is thus demonstrated that phenol can be produced from benzene as a primary reactant and oxygen and hydrogen as secondary reactants without producing acetone by-product by combining a series of steps of:
(a) reacting benzene with propylene to synthesize cumene,
(b) oxidizing the cumene of step (a) into cumene hydroperoxide,
(c) acid cleaving cumene hydroperoxide into phenol and acetone,
(d) hydrogenating the acetone of step (c) into isopropanol,
(e) dehydrating the isopropanol of step (d) into propylene, and
(f) recycling the propylene of step (e) to step (a).

According to the present invention, phenol can be effectively produced from benzene via a hydrocarbon having 3 carbon atoms as an intermediate by combining the above-defined steps (a) to (f), eliminating a need for paying attention to the commercial demand for acetone which is otherwise produced as a by-product in the prior art cumene process.

Propylene can be produced from the acetone by-product produced upon preparation of phenol by combining the above-defined steps (a) to (e). Thus prepared propylene is useful by itself for any other uses.

Although some preferred embodiments have been described, many modifications and variations may be made thereto in the light of the above teachings. It is therefore to be understood that within the scope of the appended claims, the invention may be practiced otherwise than as specifically described.

What is claimed:
1. A process for preparing phenol, comprising the steps of:
(a) reacting benzene with propylene in the presence of an aluminum chloride complex at a temperature in the range of from 30° C. to 200° C. under a pressure from atmospheric pressure to 15 kg-f/cm$^2$ to synthesize cumene, said benzene and said propylene being used in a molar ratio of from 1/1 to 10/1;
(b) oxidizing the cumene of step (a) with molecular oxygen at a temperature in the range of from 60° C. to 150° C. under a pressure of from 1 to 10 kg-f/cm$^2$ to convert the cumene into cumene hydroperoxide;
(c) acid cleaving cumene hydroperoxide into phenol and acetone with an acidic compound selected from the group consisting of strong acids, heteropolyacids, and solid acids at a temperature of up to 150° C.;
(d) hydrogenating the acetone of step (c) with hydrogen gas by a fixed bed liquid phase reaction in the presence of a hydrogenation catalyst selected from the group consisting of Raney nickel, nickel, copper-chromium, Raney nickel-copper, copper-zinc, platinum, palladium, ruthenium and rhodium, said catalyst optionally supported on a carrier, at a temperature of from room temperature to 200° C. under a pressure of from atmospheric pressure to 80 kg-f/cm$^2$, to convert the acetone into isopropanol, said hydrogen and said acetone being used in molar ratio of from 1/2 to 10/1;
(e) dehydrating the isopropanol of step (d) into propylene in the presence of an acidic compound at a temperature in the range of from 100° C. to 450° C. under reduced, atmospheric or increased pressure; and

(f) recycling the propylene of step (e) in a liquid state to step (a).

2. The process of claim 1, wherein step (f) includes pressurizing the propylene of step (e) and recycling the propylene to step (a).

3. A process for recovering propylene from the acetone by-produced during the preparation of phenol, comprising the steps of:

(a) reacting the benzene with propylene in the presence of an aluminum chloride complex at a temperature in the range of from 30° C. to 200° C. under a pressure of from atmospheric pressure to 15 kg-f/cm$^2$ to synthesize cumene, said benzene and said propylene being used in a molar ratio of from 1/1 to 10/1;

(b) oxidizing the cumene of step (a) with molecular oxygen at a temperature in the range of from 60° C. to 150° C. under a pressure of from 1 to 10 kg-f/cm$^2$ to convert the cumene into cumene hydroperoxide;

(c) acid cleaving cumene hydroperoxide into phenol and acetone with an acidic compound selected from the group consisting of strong acids heteropolyacids, and solid acids at a temperature of up to 150° C.;

(d) hydrogenating the acetone of step (c) with hydrogen gas by a fixed bed liquid phase reaction in the presence of hydrogenation catalyst selected from the group consisting of Raney nickel, nickel, copper-chromium, Raney nickel-copper, copper-zinc, platinum, platinum, palladium, ruthenium and rhodium, said catalyst optionally supported on a carrier at a temperature of from room temperature to 200° C. under a pressure of from atmospheric pressure to 80 kg-f/cm$^2$, to convert the acetone being used at a molar ratio of from 1/2 to 10/1; and (e) dehydrating the isopropanol of step (d) into propylene in the presence of an acidic compound at a temperature in the range of from 100° C. to 450° C. under reduced, atmospheric or increased pressure.

4. The process of claim 3, wherein steps (a), (b), and (c) are included in the cumene process for the synthesis of phenol and acetone.

5. The process of claim 3, wherein step (f) includes cooling the propylene of step (e) and recycling the propylene to step (a).

* * * * *